United States Patent [19]

Osberghaus et al.

[11] 4,143,160

[45] Mar. 6, 1979

[54] PROCESS FOR MOISTURING THE SKIN

[75] Inventors: Rainer Osberghaus, Dusseldorf-Urdenbach; Peter Lorenz, Langenfeld; Christian Gloxhuber, Haan; Siegfried Braig, Hilden, all of Fed. Rep. of Germany

[73] Assignee: Henkel Kommanditgesellschaft auf Aktien, Dusseldorf, Fed. Rep. of Germany

[21] Appl. No.: 743,473

[22] Filed: Nov. 19, 1976

Related U.S. Application Data

[63] Continuation of Ser. No. 544,811, Jan. 28, 1975, abandoned.

[30] Foreign Application Priority Data

Jan. 29, 1974 [DE] Fed. Rep. of Germany ....... 2404071

[51] Int. Cl.$^2$ ............................................ A61K 47/00
[52] U.S. Cl. ..................................... 424/365; 424/59; 424/73
[58] Field of Search .......................................... 424/365

[56] References Cited

U.S. PATENT DOCUMENTS

| 2,075,107 | 3/1937 | Frazier | 260/404 |
| 2,311,008 | 2/1943 | Tucker | 260/535 P |
| 3,198,828 | 8/1965 | Matter | 424/65 X |
| 3,293,176 | 12/1966 | White | 260/535 P |
| 3,373,173 | 3/1968 | Foley et al. | 260/404 |
| 3,399,179 | 8/1968 | Grakauskas | 260/535 P X |
| 3,725,290 | 4/1973 | Nelson et al. | 260/535 P |
| 3,839,399 | 10/1974 | Starks et al. | 260/404 X |

FOREIGN PATENT DOCUMENTS

| 127M | 2/1961 | France | 424/315 |
| 2451M | 4/1964 | France | 424/315 |
| 1447188 | 6/1966 | France | 424/365 |

OTHER PUBLICATIONS

Rothe et al., Chem. Abs.; 1971, vol. 75, p. 67498k.
Maeda et al., Chem. Abs.; 1971, vol. 75, 1971, p. 40448g.
Ghielmetti et al., Chem. Abs.; 1971, vol. 74, p. 67730j.
Ely, Chem. Abs.; 1970, vol. 73, p. 102043r.

Primary Examiner—Dale R. Ore
Attorney, Agent, or Firm—Hammond & Littell

[57] ABSTRACT

Skin-care and skin-protection agent compositions containing at least one aliphatic polycarboxylic acid, or a salt thereof, which may be substituted by sulfonate groups, as a skin moisture-retaining agent, as well as a process for protecting the skin utilizing this composition.

7 Claims, No Drawings

PROCESS FOR MOISTURING THE SKIN

This is a continuation of Ser. No. 544,811, filed Jan. 28, 1975, now abandoned.

THE PRIOR ART

It is generally known that the protective measures for healthy skin include, among other things, that the skin surface maintains a certain hygroscopicity. The skin substances upon which this hygroscopicity and its constant restoration depend may be removed from the skin by environmental influences, such as repeated washing with substances which have a strong wetting and extracting effect, and by the influence of chemicals or severe weather. This removal produces alterations in the horny layer which can greatly reduce the protective action of the skin against harmful environmental influences.

OBJECTS OF THE INVENTION

It is an object of the present invention to provide a skin-care and skin-protection agent composition containing at least one aliphatic polycarboxylic acid, or a salt thereof, which may be substituted by sulfonate groups, as a skin moisturizing agent.

It is another object of the present invention to provide a skin-care and skin-protection agent composition, by means of which the functional capacity of the skin may be maintained or increased in spite of harmful environmental influences, and which effectively supports the restoration of the horny layer, should any damage have been incurred.

These and further objects of the invention will become apparent as the description thereof proceeds.

DESCRIPTION OF THE INVENTION

The present invention relates to skin-care and skin-protection agent compositions containing at least one aliphatic polycarboxylic acid, or a salt thereof, which may be substituted by sulfonate groups, as a skin moisturizing agent.

Accordingly the present invention provides skin-care and skin-protection agent compositions comprising conventional constituents, such as emulsifiers, fatty substances, plant extracts, solvents, perfumes, thickeners and preservatives, as well as at least one aliphatic polycarboxylic acid, or a salt thereof, possibly substituted by sulfonate groups, of the formula

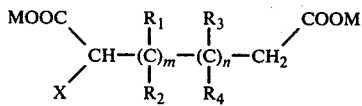

in which M represents hydrogen, an alkali metal cation, an alkaline earth metal cation, ammonium, alkyl substituted ammonium or alkylol substituted ammonium, X represents hydrogen, —COOM, or —SO$_3$M, R$_1$, R$_2$, R$_3$ and R$_4$ each represent hydrogen or —COOM, in which M has the above-described meanings, and m and n are each the integer 0, 1 or 2, in a quantity of 1% to 20% by weight, preferably 3% to 10% by weight, based upon the total weight of the composition.

More particularly, the present invention provides a cosmetic agent composition for the care and protection of the skin of warm-blooded animals consisting essentially of from 1% to 20% by weight based upon the total weight of at least one aliphatic polycarboxylic acid compound of the formula

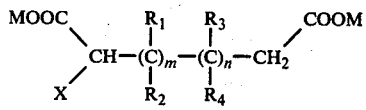

wherein

M is selected from the group consisting of hydrogen, alkali metal, alkaline earth metal, ammonium, loweralkylammonium and loweralkylolammonium, X is selected from the group consisting of hydrogen, —COOM and —SO$_3$M in which M has the above-defined meanings, R$_1$, R$_2$, R$_3$ and R$_4$ are each selected from the group consisting of hydrogen and —COOM in which M has the above-defined meanings, and m and n are each the integer 0, 1 or 2; and the remainder inert cosmetic excipients.

In addition the present invention provides an improvement in a process for the care and protection of the skin of warm-blooded animals comprising topically applying to the skin a safe but effective amount of the above-mentioned agent composition.

The polycarboxylic acids which are used in the agent compositions of the invention are extremely suitable for maintaining or restoring the water retention of the skin and thus for keeping the skin soft, supple and fully capable of performing its function.

These acids can be produced according to generally known processes. Thus, the disodium salt of sulfo-succinic acid can be produced in accordance with the information given by R. Messel in Liebigs Annalen der Chemie 157, (1871) page 15, by direct addition of sodium sulfite to maleic acid.

The sodium salts, which have not been described hitherto, of propane-1,1,2,3-tetracarboxylic acid, butane-1,2,2,3,4-pentacarboxylic acid and butane-1,2,2,3,3,4-hexcarboxylic acid can be obtained from esters, which are known from publications, by direct saponification with sodium hydroxide. The appropriate free acids can be obtained from the salts by treatment with acid ion exchangers. the propane-1,1,2,3-tetracarboxylic acid tetraethyl ester, which is required as intermediate product, can be obtained, according to the information given by H. T. Clarke and T. F. Murray in Organic Syntheses Collective Vol. 1 (1932), page 272, by reaction of diethyl fumarate with diethyl malonate. The esters of butane-1,2,2,3,4-pentacarboxylic acid and of butane-1,2,2,3,3,4-hexacarboxylic acid, which are required as intermediate products, are obtained, according to the information given by S. Buchta and K. Greiner, Chemische Berichte 94 (1961), page 1311, and C. A. Bischoff, Chemische Berichte 16 (1883), page 1044, by Michael-Addition of triethyl ethane-1,1,2-tricarboxylate to diethyl maleate, or alternatively by oxidative dimerization of triethyl ethane-1,1,2-tricarboxylate.

The pentane-1,2,3,4,5-pentacarboxylic acid can be prepared by alkaline saponification of the hexamethyl pentane-1,2,2,3,4,5-hexacarboxylate and treatment of the reaction solution with an acid ion exchanger. The hexamethyl ester is obtained by converting the trimethyl ethane-1,1,2-tricarboxylate, produced in accordance with the information given by B. Bischoff Chemische Berichte 29 (1896), page 967, into the sodium salt and by reacting it with trimethyl aconitate.

The hexane-1,2,3,4,5,6-hexacarboxylic acid can be prepared by alkaline saponification of the octamethyl hexane-1,2,3,3,4,4,5,6-octacarboxylate and by treatment of the reaction solution with an acid ion exchanger. For the production of the octamethyl ester, the tetramethyl propane-1,1,2,3-tetra-carboxylate, obtained from dimethyl malonate and dimethyl fumarate in accordance with the information given in Organic Syntheses, Coll Vol. 1, page 272, is oxidatively dimerized in aqueous solution by means of cerium-(IV)-sulfate.

Examples of suitable aliphatic polycarboxylic acids, some of which have sulfonate groups, for use in accordance with the invention, are succinic acid, sulfo-succinic acid, glutaric acid, adipic acid, pimelic acid, suberic acid, propane-1,1,2,3-tetracarboxylic acid, butane-1,2,2,3,4-pentacarboxylic acid, butane-1,2,2,3,3,4-hexacarboxylic acid, pentane-1,2,3,4,5-pentacarboxylic acid and hexane-1,2,3,4,5,6-hexacarboxylic acid. The polycarboxylic acids which have from 3 to 6 acid groups are particularly preferred. There can be one sulfonic acid and two carboxylic acid groups or greater numbers of either sulfonic acid or carboxylic acid groups up to a total of six. They are predominantly used in the form of their pharmacologically acceptable salts in the skin-care and skin-protection agent compositions.

Suitable examples of the nontoxic pharmacologically acceptable salts of the aliphatic, polycarboxylic acids are the alkali metal salts such as sodium or potassium, alkaline earth metal salts, ammonium, loweralkylammonium salts such as methylammonium, ethylammonium, propylammonium, isopropylammonium, dimethylammonium, diethylammonium, loweralkylolammonium salts such as monoethanolammonium, diethanolammonium, triethanolammonium, and isopropanolammonium. the alkali metal salts are preferred and the sodium salts are especially preferred.

All the above-mentioned acids or their salts are colorless, odorless and completely stable products, which possess excellent physiological compatibility and have no disadvantageous effects on the skin-care and skin-protection agent composition with which they are mixed.

The compounds which are to be used in accordance with the invention are characterized by their good water absorption capacity and also by their excellent water retention capacity. Owing to these properties and their good physiological compatibility they are highly suitable as skin humectants in cosmetic preparations, in particular in agents for the care and protection of the skin.

It is known that in addition to other factors a certain hygroscopicity is necessary for the protection of a healthy skin. If the skin is deprived of the substances which are responsible for this hygroscopicity as well as its continual restoration by environmental circumstances such as repeated washings, effect of chemicals or strong weather influences, alterations occur in the stratum corneum, as a result of which the protective effect of the skin against harmful influences of the environment may be considerably diminished.

It was found that the functional capacity of the skin may be maintained or restored even to a higher degree than before if it is treated with agents for the care and protection of the skin, which besides the customary constituents include from 1% to 20% by weight, preferably 3% to 10% by weight, based on the total composition of the aliphatic polycarboxylic acids optionally containing sulfonate groups, or salts, in accordance with the invention.

Among the compositions for the care and protection of the skin having special skin-caring properties due to the addition of the said aliphatic polycarboxylic acids optionally containing sulfonate groups used in accordance with the invention or their physiologically-compatible salts are emulsions of oil-in-water or water-in-oil type. These are the conventional day creams, baby creams, night creams and nourishing creams, cleansing creams, skin protection creams, glycerol creams, creams with special additives of animal or vegetable origin, sun protection or sun tanning creams, and sun protecton emulsions, face lotions and after-shave lotions. The incorporation of the agents for care and protection of the skin may take place in the known manner by simple stirring-in or dissolving. In addition to the aliphatic polycarboxylic acids optionally substituted by sulfonate groups, or salts used in accordance with the invention, the cosmetic preparations may contain the constituents normally present in them such as emulsifiers, fatty substances, plant extracts, preservatives, perfumes, solvents, thickeners and preservatives in the customary amounts. The pH value of the agents for the care and protection of the skin may be in the acid to neutral region (pH 5 – 7.0) and is approximately adjusted to weakly acid values of about pH 6.

The following examples are intended to illustrate the subject of the invention without, however, limiting it to these examples.

EXAMPLES

Several of the aliphatic polycarboxylic acids, which are possibly substituted by sulfonate groups and which can be used as skin moisture-retaining agents in the skin-care and skin-protecting agent compositions of the invention, are first of all to be mentioned.

EXAMPLE A

Tetra-sodium salt of propane-1,1,2,3-tetracarboxylic acid, water of crystallization content 13%.

The propane-1,1,2,3-tetracarboxylic acid-tetraethylester, which was obtained according to the information given by H. T. Clarke and T. F. Murray in Organic Syntheses Collective Vol. 1 (1932), page 272 by reaction of diethyl fumarate with diethyl malonate, was boiled with sufficient 20% aqueous-alcoholic (1 : 1) sodium hydroxide for a pH value of 9 to be retained even when boiled for a considerable period of time. The amount of sodium hydroxide calculated for the neutralization was also used therein. The clear reaction solution was the evaporated to dryness and the solid body which was obtained was dried in vacuum over phosphorus pentoxide.

EXAMPLE B

Penta-sodium salt of butane-1,2,2,3,4-pentacarboxylic acid, water crystallization content 6.5%.

The salt was produced utilizing a procedure analogous to that described for Product A by saponification of the pentaethyl butane-1,2,2,3,4-pentacarboxylate, which was obtained by Michael-Addition of triethyl ethane-1,1,2-tricarboxylate to diethyl maleate.

EXAMPLE C

Hexa-sodium salt of butane-1,2,2,3,3,4-hexacarboxylic acid, water of crystallization content 10%.

This salt was prepared utilizing a procedure analogous to that described for Product A by saponification of the hexaethyl butane-1,2,2,3,3,4-hexacarboxylate, which was obtained by oxidative dimerization of triethyl ethane-1,1,2-tricarboxylate.

EXAMPLE D

Tri-sodiium salt of sulfo-succinic acid.

This is a known salt as described above.

The favorable action of the compounds, which are to be used in accordance with the invention, with regard to capacity for the absorption and retention of water, was determined by means of test methods which are described more fully hereinafter. A process for determining the equilibrium dampness, which constitutes a gauge for the water retention capacity, and the determination of the water retention, rehydration and elasticity of impregnated pig epidermis is described in these tests.

1. Determination of the equilibrium dampness

The substances (about 300 to 500 mg) to be tested were moistened with a defined quantity of water and exposed for 24 hours at 23° C. to various relative atmospheric humidities (1%, 30%, 47%, 65%, 89% and 100% relative humidity). The amount of water absorbed or desorbed was determined gravimetrically and plotted on a graph. The relative humidity at which neither expulsion nor retention of water is effected, can be determined from the resultant curves. This value, which is designated as the equilibrium dampness, is a gauge for the water retention capacity of a substance. The lower the value, the more positive should be the assessment of the product. The steepness of the curve, in addition, indicated the water retaining capacity (hygroscopicity) of the substance.

2. Tests on the pig epidermis (a) To obtain the pig epidermis

As soon as the pigs have been killed, the bristles of the skin are cut off by means of a shearing machine (shearing head of 0.1 mm). The pigs are soaked for 3 to 5 minutes in warm water of 60°C., the epidermis is then peeled off and stored at −20° C. until used.

(b) Determination of the water retention and the rehydration of impregnated pig epidermis.

Stamped cut pieces of epidermis (1× 2 cm) were soaked for 2 hours in a 10% solution of the test substance, excess moisture was removed by means of a small press under standardized conditions and the pieces were dried for 24 hours, hanging free between 2 clamps in a 100 ml Erlenmeyer flask at 23° C. both at 30% relative humidity and 50% relative humidity (set by sulfuric acid/water mixtures). The drying out of the impregnated test pieces to X% of the initial weight was compared with the corresponding value of the epidermis which has been soaked only in water (blank value). In Table I, the improvement in the water retention and the rehydration as compared with the blank value is given in δ% of $H_2O$. The deviations in each double test amounted to a maximum of ± 2 absolute units. If greater deviations occurred, the test was repeated. The rehydration was determined analogously by drying the pig epidermis, which had been impregnated and from which the excess moisture had been removed, for 24 hours at 30% relative humidity, and by subsequent 24-hour incubation at 90% relative humidity.

(c) Gauging of elasticity of impregnated pig epidermis

Stamped out pieces of pig epidermis (1 × 6 cm) were soaked for 2 hours in a 10% aqueous solution of the substance which was to be tested, and excess moisture was removed from these pieces under standardized conditions. The test pieces were incubated for 24 hours, hanging free between 2 clamps both at 75% relative humidity and at 90% relative humidity and were stretched in a nipping tensile-testing machine (type: 1402) with 0 to 50 pund loading. The amount of stretch, which was measured in the Hooke range with loadings of 5 to 30 pund, was given in mm as a gauge for the elasticity.

The measured values obtained in the previously described tests can be seen hereinafter in Table I.

TABLE I

| | | Equilibrium dampness and measured values for pig epidermis Measurements from the pig epidermis | | | | |
|---|---|---|---|---|---|---|
| Product | Equilibrium dampness (% r.h.) | Water retention Δ% $H_2O$ after drying out | | Rehydration Δ% water absorption | mm stretch with between 5 and 30 pund loading | |
| | | at 30% r.h. | at 50% r.h. | at 90% r.h. | at 90% r.h. | at 75% r.h. |
| Blank value | — | 0 | 0 | 0 | 0.3 – 0.5 | 0 |
| A | 42 | 7 | 28 | 54 | 2.6 | 1.0 |
| B | 48 | 2 | 16 | 35 | 4.0 | 1.1 |
| C | 44 | 15 | 18 | 46 | 3.2 | 0.6 |
| D | — | 13 | 20 | 29 | 1.7 | 0.4 |

"—" = was not measured

These aforementioned measured values of Table I confirm the suitability of the products which are to be used in accordance with the invention as skin moisture-containing agents, particularly in the form of their sodium salts, in skin care and skin protection agents.

The following are a few examples of cosmetic preparations containing substances in accordance with the invention as skin humectants.

EXAMPLE 1

| Day cream, slightly greasy | Parts by weight |
|---|---|
| Fatty acid partial glyceride Cutina MD® Dehydag | 6.0 |
| Stearic acid | 8.0 |
| Mixture of nonionic emulsifiers Emulgin C 700® Dehydag | 3.0 |
| 2-octyl-dodecanol | 4.0 |
| Vegetable oil | 3.0 |
| Paraffin oil | 5.0 |
| Triethanolamine | 0.4 |
| 1,2-propylene glycol | 3.0 |
| Product A | 3.0 |
| Nipagin M | 0.2 |
| Perfume oil | 1.0 |

EXAMPLE 1-continued

| Day cream, slightly greasy | Parts by weight |
|---|---|
| Water | 63.4 |

EXAMPLE 2

| Baby cream | Parts by Weight |
|---|---|
| Mixture of higher molecular esters, mainly mixed esters of pentaerythritol fatty acid ester and citric acid fatty alcohol ester Dehymuls E® Dehydag | 7.0 |
| Decyl oleate | 10.0 |
| Vaseline® | 10.0 |
| Wool fat | 5.0 |
| Boric acid | 0.2 |
| Talcum | 12.0 |
| Zinc oxide | 8.0 |
| Nipagin M | 0.2 |
| Product B | 5.0 |
| Water | 42.6 |

EXAMPLE 3

| Night cream | Parts by Weight |
|---|---|
| Colloidally dispersed mixture of 90 parts of cetyl-stearyl alcohol and 10 parts of sodium lauryl sulfate | 10.0 |
| 2-Octyl-dodecanol | 12.0 |
| Vegetable oil | 7.0 |
| Wool fat | 2.0 |
| Glycerol | 1.0 |
| Product C | 5.0 |
| Nipagin M | |
| Perfume Oil | 1.0 |
| Water | 61.8 |

EXAMPLE 4

| Boro-glycerol cream | Parts by Weight |
|---|---|
| Colloidally dispersed mixture of 90 parts of cetyl-stearyl alcohol and 10 parts of sodium lauryl sulfate | 12.0 |
| 2-Octyl-dodecanol | 8.0 |
| Vegetable oil | 5.0 |
| Boric acid | 2.0 |
| Glycerol | 28.0 |
| Nipagin M | 0.2 |
| Product A | 3.0 |
| Water | 41.8 |

EXAMPLE 5

| Sun protection cream | Parts by Weight |
|---|---|
| Mixture of higher molecular esters with fatty substances Dehymuls K ® Dehydag | 30.0 |
| Decyl oleate | 15.0 |
| Light protection agent | 5.0 |
| Nipagin M | 0.2 |
| Product D | 3.0 |
| Water | 46.8 |

EXAMPLE 6

| Face mask | Parts by Weight |
|---|---|
| Mixtures of fatty acid partial glyceride with emulsifiers Cutina LE ®Dehydag | 12.0 |
| Decyl oleate | 4.0 |
| Vitamin oil | 5.0 |
| Kaolin | 2.0 |
| Rice starch | 3.0 |
| Nipagin M | 0.2 |
| Product B | 6.0 |
| Water | 67.8 |

EXAMPLE 7

| After-shave lotion | Parts by Weight |
|---|---|
| Oleyl/cetyl alcohol | 1.0 |
| Ethanol 96% | 67.5 |
| Menthol | 0.2 |
| Camphor | 0.2 |
| Peru balsam | 0.1 |
| Perfume | 0.5 |
| Hammamelis extract | 10.0 |
| Boric acid | 0.5 |
| Product D | 10.0 |
| Water | 10.0 |

EXAMPLE 8

| Face lotion | Parts by Weight |
|---|---|
| Cucumber essence | 15.0 |
| Citric acid | 0.2 |
| Ethanol 96% | 15.0 |
| Product C | 10.0 |
| Perfume | 1.0 |
| Water | 58.8 |

In place of the compounds used in accordance with the invention mentioned in the above examples, others of the products in accordance with the invention may be used with equally good success.

The preceding specific embodiments are illustrative of the practice of the invention. It is to be understood, however, that other expedients known to those skilled in the art, or given herein, may be employed without departing from the spirit of the invention or the scope of the appended claims.

We claim:

1. A process for the care and protection of the skin of warm-blooded animals comprising topically applying to the skin a safe but effective amount as a moisturizing agent of a cosmetic moisturizing composition consisting essentially of an emulsion adjusted to a pH between 5 and 7 containing an emulsifier, from 1% to 20% by weight based upon the total weight of at least one aliphatic polycarboxylic acid compound of the formula

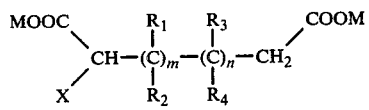

wherein

M is selected from the group consisting of hydrogen, alkali metal, alkaline earth metal, ammonium, loweralkylammonium and loweralkylolammonium, X is selected from the group consisting of hydrogen, — COOM and —SO$_3$M in which M has the above-defined meanings, R$_1$, R$_2$, R$_3$ and R$_4$ are each selected from the group consisting of hydrogen and — COOM in which M has the above-defined meanings, and m and n are each the integer 0, 1 or 2; and the remainder inert cosmetic excipients, said emulsion being selected from the group consisting of an oil-in-water emulsion and a water-in-oil emulsion.

2. The process of claim 1 wherein at least one aliphatic polycarboxylic acid compound is present in an amount of from 3% to 10% by weight.

3. The process of claim 1 wherein said aliphatic polycarboxylic acid compound has from three to six acid groups.

4. The process of claim 1 wherein M is alkali metal.

5. The process of claim 1 wherein M is sodium.

6. The process of claim 1 wherein the pH is 6.

7. A process for the care and protection of the skin of warm-blooded animals comprising topically applying to the skin a safe but effective amount as a moisturizing agent of a cosmetic moisturizing composition consisting essentially of a water and ethanol solution adjusted to a pH between 5 and 7 containing from 1% to 20% by weight of at least one aliphatic polycarboxylic acid compound of the formula

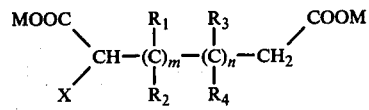

wherein
  M is selected from the group consisting of hydrogen, alkali metal, alkaline earth metal, ammonium, loweralkylammonium and loweralkylolammonium,
  X is selected from the group consisting of hydrogen, —COOM and —$SO_3M$ in which M has the above-defined meanings,
  $R_1$, $R_2$, $R_3$ and $R_4$ are each selected from the group consisting of hydrogen and —COOM in which M has the above-defined meanings, and
  m and n are each the integer 0, 1 or 2; and
  the remainder inert cosmetic excipients.

* * * * *